United States Patent
Loomis

(12) 
(10) Patent No.: US 6,403,758 B1
(45) Date of Patent: Jun. 11, 2002

(54) BIORESORBABLE COMPOSITIONS FOR IMPLANTABLE PROSTHESES

(75) Inventor: Gary L. Loomis, Morristown, NJ (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/436,774

(22) Filed: Nov. 8, 1999

Related U.S. Application Data

(60) Continuation of application No. 09/243,379, filed on Feb. 1, 1999, now Pat. No. 6,028,164, which is a continuation of application No. 09/145,588, filed on Sep. 2, 1998, now Pat. No. 6,005,020, which is a division of application No. 08/914,130, filed on Aug. 18, 1997, now Pat. No. 5,854,382.

(51) Int. Cl.⁷ .................. A61L 27/00; A61L 29/00; A61L 31/00; A61F 2/12
(52) U.S. Cl. .................. 528/354; 528/361; 424/401; 424/422; 424/423; 424/424; 424/426; 424/430; 424/433; 424/480; 525/54.1; 525/408; 525/413; 525/415; 525/772.1; 525/772.2; 514/773; 514/777; 523/105; 523/111; 523/113; 623/8; 623/11
(58) Field of Search .................. 528/354, 361; 424/401, 422, 423, 424, 426, 430, 433, 480; 525/54.1, 408, 413, 415, 772.1, 772.2; 514/773, 777; 523/105, 111, 113; 623/8, 11

(56) References Cited

U.S. PATENT DOCUMENTS

| | | |
|---|---|---|
| 4,321,711 A | 3/1982 | Mano |
| 4,438,253 A | 3/1984 | Casey et al. |
| 4,704,131 A | 11/1987 | Noishiki et al. |
| 4,826,945 A | 5/1989 | Cohn et al. |
| 4,842,575 A | 6/1989 | Hoffman, Jr. et al. |
| 5,034,265 A | 7/1991 | Hoffman et al. |
| 5,202,413 A | 4/1993 | Spinu |
| 5,410,016 A | 4/1995 | Hubbell et al. |
| 5,415,619 A | 5/1995 | Lee et al. |
| 5,529,914 A | 6/1996 | Hubbell et al. |
| 5,567,440 A | 10/1996 | Hubbell et al. |
| 5,573,934 A | 11/1996 | Hubbell et al. |
| 5,584,875 A | 12/1996 | Duhamel et al. |
| 5,854,382 A | * 12/1998 | Loomis ............ 528/354 |
| 6,005,020 A | * 12/1999 | Loomis ............ 523/105 |
| 6,028,164 A | * 2/2000 | Loomis ............ 528/354 |

FOREIGN PATENT DOCUMENTS

| | | |
|---|---|---|
| EP | 0 230 635 | 8/1987 |
| EP | 0 271 216 | 6/1988 |
| EP | 0 486 294 A2 | 5/1992 |
| EP | 0 841 360 A | 5/1998 |
| WO | WO 92/09311 | 6/1992 |
| WO | WO 95/01190 | 1/1995 |

OTHER PUBLICATIONS

Morphological Study of Biodegradable PEO/PLA Block Copolymers, Hani Younes and Daniel Cohn, *Journal of Biomedical Materials Research*, vol. 21, pp. 1301–1316 (1987).

Biodegradable PEO/PLA Block Copolymers, Daniel Cohn and Hani Younes, *Journal of Biomedical Materials Research*, vol. 22, pp. 993–1009 (1988).

Biodegradable Hydrogels Based on Photopolymerized Poly(ethylene glycol)–co–poly($\alpha$–hydroxy acid) Diacrylate Macromers, Amarpreet S. Sawhney; Chandrashekhar P. Pathak; and Jeffrey A. Hubbell, *Macromolecules*, vol. 26, p. 581–587 (1993).

*Biodegradable Hydrogels For Drug Delivery*, Kinam Park, Waleed S.W. Shalaby and Hue Sun Park, Technomic Publishing Co. Publishers (1993).

\* cited by examiner

*Primary Examiner*—Nathan M. Nutter
(74) *Attorney, Agent, or Firm*—Hoffman & Baron, LLP

(57) ABSTRACT

Crosslinked compositions formed from a water-insoluble copolymer are disclosed. These compositions are copolymers having a bioresorbable region, a hydrophilic region and at least two crosslinkable functional groups per polymer chain. These compositions are able to form hydrogels in aqueous environments when crosslinked. These hydrogels are good sealants for implantable prostheses when in contact with an aqueous environment. In addition, such hydrogels can be used as delivery vehicles for therapeutic agents.

22 Claims, No Drawings

BIORESORBABLE COMPOSITIONS FOR IMPLANTABLE PROSTHESES

This application is a continuation of copending U.S. application Ser. No. 09/243,379, filed on Feb. 1, 1999, expressly incorporated by reference herein, now U.S. Pat. No. 6,028,164, which is a continuation of copending U.S. application Ser. No. 09/145,588, filed on Sep. 2, 1998, expressly incorporated by reference herein, now U.S. Pat. No. 6,005,020, which is a divisional of U.S. application Ser. No. 08/914,130, filed on Aug. 18, 1997, expressly incorporated by reference herein, now U.S. Pat. No. 5,854,382.

FIELD OF INVENTION

This invention relates generally to coating compositions for medical devices. More particularly, the present invention relates to cross-linked compositions formed from a water insoluble copolymer having a bioresorbable region, a hydrophilic region and at least two cross-linkable functional groups per polymer chain. These compositions when placed in contact with an aqueous environment form hydrogels which are useful as sealants for porous materials and particularly for implantable prostheses. Furthermore, these hydrogels can be used as delivery vehicles for therapeutic agents. Medical devices coated and/or sealed with such hydrogels, processes for forming such devices and methods of making the hydrogels are also disclosed.

BACKGROUND OF THE INVENTION

It is generally known to provide a porous substrate, such as an implantable prosthesis, with a biocompatible, biodegradable sealant or coating composition which initially renders the porous substrate fluid-tight. Over time, such a sealant composition is resorbed and the healing process naturally takes over the sealing function of the sealant composition as tissue ingrowth encapsulates the prosthesis. The art is replete with examples of naturally derived, as well as chemically synthesized sealant compositions.

Natural materials, such as collagen and gelatin, have been widely used on textile grafts. U.S. Pat. Nos. 4,842,575 and 5,034,265 to Hoffman Jr., et al. disclose the use of collagen as a sealant composition for grafts. More recently, co-owned and co-pending U.S. Ser. No. 08/713,801 discloses the use of a hydrogel or sol-gel mixture of polysaccharides for rendering fluid-tight porous implantable devices. Such sealant compositions are beneficial in that they are able to seal an implantable device without the need for chemical modification of the surface thereof and provide improved bioresorbability as the healing process occurs. Furthermore, fibrin, an insoluble protein formed during the blood clotting process, has also been used as a sealant for porous implantable devices.

The use of such biologically derived sealant compositions, however, suffers from several drawbacks. One such drawback is the difficulty in producing consistent coatings due to variations inherent in natural materials. Another drawback is that the body may identify such compositions as foreign and mount an immune response thereto. Thus, biologically-based sealant compositions can cause inflammation, as well as infection at or around the site of implantation, which can lead to life-threatening complications.

Accordingly, attempts have been made to design sealant systems from chemically synthesized materials which are easier to manufacture and control the desired characteristics and qualities and which have less potential for causing adverse biological reactions. For example, U.S. Pat. No. 4,826,945 to Cohn et al. discloses synthetically produced resorbable block copolymers of poly($\alpha$-hydroxy-carboxylic acid)/poly(oxyalkylene) which are used to make absorbable sutures, wound and burn dressings and partially or totally biodegradable vascular grafts. These copolymers, however, are not crosslinked. The poly(alkylene) segments of such bio-absorbable copolymers are disclosed to be water-soluble so that the body can excrete the degraded block copolymer compositions. See also, Younes, H. and Cohn, D., *J. Biomed. Mater. Res.* 21, 1301–1316 (1987) and Cohn, D. and Younes, H., *J Biomed. Mater. Res.* 22, 993–1009 (1988). As set forth above, these compositions are uncrosslinked and, as a consequence, are relatively quickly bio-absorbed. Moreover, these uncrosslinked compositions generally require the presence of crystalline segments to retain their hydrogel-like consistency. As a result of such crystalline segments, these compositions have limited utility as sealants for vascular grafts.

Furthermore, U.S. Pat. No. 4,438,253 to Casey et al. discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as, tetra-p-tolyl orthocarbonate into the copolymer structure. The strength and flexibility which makes such a composition useful as a suture, however, does not necessarily make it appropriate for use as a sealant for a porous implantable prosthesis. Moreover, these tri-block copolymers are substantially uncross-linked. Thus, while compositions are somewhat hydrophilic, they do not form hydrogels.

Accordingly, attempts have been made to engineer biocompatible hydrogel compositions whose integrity can be controlled through crosslinking. For example, U.S. Pat. Nos. 5,410,016 and 5,529,914 to Hubbell et al. disclose water-soluble systems which when crosslinked utilize block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly (a-hydroxy acid), such as, polyglycolic acid or polylactic acid. See, Sawhney, A. S., Pathak, C. P., Hubbell, J. A., *Macromolecules* 1993, 26, 581–587.

Furthermore, U.S. Pat. No. 5,202,413 to Spinu discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane. The general structure of such a composition is R-(A-B-A-L)$_x$-A-B-A-R, where A is a polyhydroxy acid, such as polylactide, polyglycolide or a copolymer thereof, B is an oligomeric diol or diamine residue, L is a diacyl residue derived from an aromatic diacyl halide or diisocyanate and R is H or an end-capping group, such as an acyl radical. A major difference between the compositions set forth in the Spinu '413 patent and those described by the Cohn references supra is that Spinu uses lactide blocks whereas Cohn uses lactic acid blocks. Furthermore, like the Cohn copolymers, the copolymers described in the Spinu '413 patent are not crosslinkable.

In general, all of the synthetic compositions set forth above describe copolymers having one or more segments which are water-soluble. Accordingly, many of the compositions described by these references are intended to be rapidly biodegraded by the body.

Thus, there is a need for water-insoluble, fully crosslinkable polymeric materials which are easily synthesized and provide controlled bioresorption in vivo. Moreover, there is a need for improved, cost-efficient synthetic sealant compositions for porous implantable prostheses which are characterized by their ability to self-emulsify and form stable low viscosity emulsions. There is a further need for sealant compositions which are quickly cured, exist as hydrogels in an aqueous environment and which remain flexible while dehydrated without the need for an external plasticizer. The present invention is directed to meeting these and other needs.

SUMMARY OF THE INVENTION

In one embodiment of the present invention, there is provided a covalently crosslinkable composition. This composition includes a water-insoluble copolymer which has a bioresorbable region, a hydrophilic region and a plurality of crosslinkable functional groups per polymer chain.

In another embodiment of the present invention, there is provided a medical device which has on at least one surface thereof a bioresorbable coating composition. This composition includes a hydrogel formed from the crosslinking of a polymer containing a bioresorbable region, a hydrophilic region, a plurality of crosslinkable functional groups and a crosslinking agent.

In a further embodiment of the present invention, there is provided a process for forming a hydrogel. This process includes providing an aqueous emulsion of a water-insoluble copolymer. This water-insoluble copolymer includes a bioresorbable region, a hydrophilic region, a plurality of crosslinkable functional groups per polymer chain and a crosslinking agent. Activation of the crosslinking agent crosslinks the copolymer composition and forms the hydrogel.

In yet a further embodiment of the present invention, there is provided a process for forming a medical device coated with a hydrogel. The hydrogel is formed from an aqueous emulsion which includes a water-insoluble copolymer having a bioresorbable region, a hydrophilic region, a plurality of crosslinkable functional groups per polymer chain and a crosslinking agent. This process includes applying the hydrogel to the medical device and then activating the crosslinking agent in a humid environment.

DETAILED DESCRIPTION OF THE INVENTION

The present invention is directed to covalently crosslinkable compositions formed from water-insoluble copolymers. The copolymers of the present invention include a bioresorbable region, a hydrophilic region and a plurality of crosslinkable functional groups per polymer chain.

When uncrosslinked, the copolymer compositions form stable aqueous emulsions. Once crosslinked, however, such compositions form hydrogels in the presence of water. Hydrogels formed from the compositions of the present invention can serve as coatings for a medical device and/or as a therapeutic agent delivery vehicle.

The copolymers of the present invention are multi-block copolymers including, for example, di-block copolymers, tri-block copolymers, star copolymers, and the like. For purposes of illustration only, a typical tri-block copolymer of the present invention may have the following general formula:

xABAx               (I)

wherein A is the bioresorbable region, B is the hydrophilic region and x is the crosslinkable functional group.

A more specific example of a copolymer useful in the present inventive compositions has the following chemical structure:

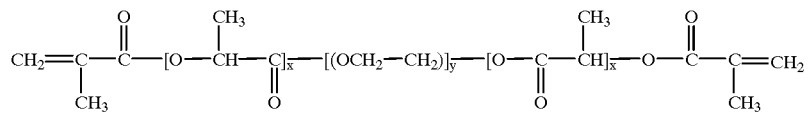

wherein x is from about 10 to about 50 and y is from about 50 to about 300, so long as the composition remains water-insoluble as a whole.

One required feature of the present invention is that the crosslinkable copolymer composition be water-insoluble. For purposes of the present invention, "water-insoluble" is intended to mean that the copolymers of the present invention are substantially insoluble in water or water-containing environments. Thus, although certain regions or segments of the copolymer may be hydrophilic or even water-soluble, however, the copolymer molecule, as a whole, does not by any substantial measure dissolve in water or water-containing environments.

As set forth above, the water-insoluble copolymer includes a bioresorbable region. For purposes of the present invention, the term "bioresorbable" means that this region is capable of being metabolized or broken down and resorbed and/or eliminated through normal excretory routes by the body. Such metabolites or break-down products should be substantially non-toxic to the body.

The bioresorbable region is preferably hydrophobic. In another preferred embodiment, however, the bioresorbable region may be designed to be hydrophilic so long as the copolymer composition as a whole is not rendered water-soluble. Thus, the bioresorbable region is designed based on the requirement that the copolymer, as a whole, must remain water-insoluble.

Accordingly, the relative properties, i.e., the kinds of functional groups contained by, and the relative proportions of the bioresorbable region, and the hydrophilic region are selected to ensure that the present compositions remain water-insoluble.

The copolymers of the present invention form a stable aqueous emulsion. For purposes of the present invention, the terms "emulsion", "emulsifiable" and "self-emulsifying" refer to the ability of the copolymers of the present composition to form an emulsion, i.e., a colloidal suspension of one liquid in another, without the requirement of an emulsifying agent to stabilize the emulsion. Although emulsifying agents are not required by the present invention, their use is not excluded in appropriate circumstances is so desired by the skilled artisan. The relative proportions or ratios of the bioresorbable and hydrophilic regions, respectively are specifically selected to render the block copolymer composition water-insoluble. Furthermore these compositions are sufficiently hydrophilic to form a hydrogel in aqueous environments when crosslinked. Such hydrogels, as set forth in more detail below, can form a fluid-tight barrier when applied to a medical device. The specific ratio of the two regions of the block copolymer composition of the present invention will of course vary depending upon the intended application and will be affected by the desired physical properties of the porous implantable prosthesis, the site of implantation, as well as other factors. For example, the composition of the present invention remains substantially water-insoluble when the ratio of the water-insoluble region to the hydrophilic region is from about 10:1 to about 1;1, on a percent by weight basis.

The bioresorbable region of the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

Based on the characteristics set forth above, a number of different compositions can be utilized as the bioresorbable region. Thus, the bioresorbable region includes without limitation, for example, poly(esters), poly(hydroxy acids), poly(lactones), poly(amides), poly(ester-amides), poly (amino acids), poly(anhydrides), poly(ortho-esters), poly (carbonates), poly(phosphazines), poly(thioesters), polysaccharides and mixtures thereof. Furthermore, the bioresorbable region can also be, for example, a poly (hydroxy) acid including poly ($\alpha$-hydroxy) acids and poly ($\beta$-hydroxy) acids. Such poly(hydroxy) acids include, for example, polylactic acid, polyglycolic acid, polycaproic acid, polybutyric acid, polyvaleric acid and copolymers and mixtures thereof As set forth above, the present composition also includes a hydrophilic region. For purposes of the present invention, "hydrophilic" is used in the classical sense of a material or substance having an affinity for water. Although the present composition contains an hydrophilic region, this region is designed and/or selected so that the composition as a whole, remains water-insoluble at all times.

When placed within the body, the hydrophilic region can be processed into excretable and/or metabolizable fragments. Thus, the hydrophilic region can include without limitation, for example polyethers, polyalkylene oxides, polyols, poly(vinyl pyrrolidine), poly(vinyl alcohol), poly (alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly (propylene) oxide and mixtures and copolymers thereof.

As set forth above, the composition of the present invention also includes a plurality of crosslinkable functional groups. Any crosslinkable functional group can be incorporated into the present compositions so long as it permits or facilitates the formation of a hydrogel. Preferably, the crosslinkable functional groups of the present invention are olefinically unsaturated groups. Suitable olefinically unsaturated functional groups include without limitation, for example, acrylates, methacrylates, butenates, maleates, allyl ethers, allyl thioesters and N-allyl carbamates. Preferably, the crosslinking agent is a free radical initiator, such as for example, 2,2'-Azobis (N,N'dimethyleneisobutyramidine) dihydrochloride.

The crosslinkable functional groups can be present at any point along the polymer chain of the present composition so long as their location does not interfere with the intended function thereof. Furthermore, the crosslinkable functional groups can be present in the polymer chain of the present invention in numbers greater than two, so long as the intended function of the present composition is not compromised.

Preferably, however, at least two olefinically unsaturated functional groups are present on the polymer chain of the present composition. As set forth above, the number of olefinically unsaturated functional groups present on the polymer chain can be increased beyond two, depending upon the particular application. Although the olefinically unsaturated functional groups can be positioned anywhere within the polymer chain of the present composition, it is preferred that at least one olefinically unsaturated functional group be positioned at a terminus of the polymer chain. More preferably, an olefinically unsaturated group is positioned at both terminal ends of the polymer chain. Furthermore, as there are at least two functional groups present in the present composition, the functional groups contained therein can be the same or different.

Crosslinking of compositions of the present invention is accomplished through the crosslinkable functional groups. These functional groups are activated to crosslink the copolymer composition by a variety of crosslinking initiators. These crosslinking initiators can include, for example, high energy radiation, thermal radiation and/or visible light. The composition of the present invention can also include free radical initiators. Such free radical initiators can include, for example, a peroxide or an azo compound.

In the present invention, the composition is crosslinked in an aqueous medium. Furthermore, when crosslinked, the copolymer composition is able to form a hydrogel. The hydrogels of the present invention are polymeric materials that swell in water without dissolving and that retain a significant amount of water in their structures. Such compositions have properties intermediate between liquid and solid states. Hydrogels also deform elastically and recover, yet will often flow at higher stresses. Thus, for purposes of this invention hydrogels are water-swollen, three-dimensional networks of hydrophilic polymers. These hydrogel compositions are not as transient as, and are more controllable than the prior art non-crosslinked sealant compositions described above. Thus, the present compositions have distinct advantages over the prior art and are able to function as superior sealants, for example, porous implantable prostheses, as well as, delivery devices for certain therapeutic agents.

In one embodiment of the invention, a therapeutic agent, such as for example a drug or bio-active agent, may be incorporated into the composition of the present invention for controlled release as the composition is bioresorbed. Thus, the present composition can be used to target therapeutic agents to specific sites in the body. Furthermore, the present composition can be engineered to bioresorb at a certain rate by controlling the ratio of the bioresorbable to the hydrophilic regions, as well as by controlling the degree of crosslinking thereof. Thus, the present compositions are able to delivery controlled quantities of a therapeutic agent to a specific site in the body as the block copolymer is bioresorbed.

Any drug or bio-active agent may be incorporated into the composition of the present invention provided that it does not interfere with the required characteristics and functions of the composition. Examples of suitable drugs or bio-active agents may include, for example, without limitation, thrombo-resistant agents, antibiotic agents, anti-tumor agents, antiviral agents, anti-angiogenic agents, angiogenic agents, anti-inflammatory agents, cell cycle regulating agents, their homologs, derivatives, fragments, pharmaceutical salts and combinations thereof.

Useful thrombo-resistant agents can include, for example, heparin, heparin sulfate, hirudin, hyaluronic acid, chondroitin sulfate, dermatan sulfate, keratin sulfate, lytic agents, including urokinase and streptokinase their homologs, analogs, fragments, derivatives and pharmaceutical salts thereof.

Useful antibiotics can include, for example, penicillins, cephalosporins, vancomycins, aminoglycosides, quinolones, polymyxins, erythromycins, tetracyclines, chloramphenicols, clindamycins, lincomycins, sulfonamides their homologs, analogs, fragments, derivatives, pharmaceutical salts and mixtures thereof.

Useful anti-tumor agents can include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide their homologs, analogs, fragments, derivatives, pharmaceutical salts and mixtures thereof.

Useful anti-viral agents can include, for example, amantadines, rimantadines, ribavirins, idoxuridines, vidarabines, trifluridines, acyclovirs, ganciclovirs, zidovudines, foscamets, interferons their homologs, analogs, fragments, derivatives, pharmaceutical salts and mixtures thereof.

In another embodiment of the present invention, there is provided a medical device having on at least one surface thereof a bioresorbable coating composition. This coating composition includes a hydrogel which is formed from the crosslinking of a polymer containing a bioresorbable region, a hydrophilic region, a plurality of crosslinked functional groups and a crosslinking agent, as set forth previously.

The bioresorbable coating composition of the present invention can be applied as coatings to medical devices. In particular, the present bioresorbable coating compositions are intended to coat medical devices made from implantable materials. These bioresorbable coatings are capable of rendering fluid-tight porous medical devices such as conduits, vascular grafts, textile materials, polymeric films and the like. For purposes of the present invention, the term "fluid-tight" refers to the specific porosity of a material, such as a porous vascular or endovascular graft. Porosity of textile materials is often measured with a Wesolowski Porosity tester. With this apparatus, a graft is tied off at one end and the free end is attached to a valve on a porometer so that the graft hangs freely in a vertical position. Then, water is run through the graft for one minute and the water that escapes from the graft is collected and measured. The specific porosity of the graft is then calculated according to the following formula:

$$P = \frac{V}{A}$$

where V is the volume of water collected in ml/min and A is the surface area of the graft exposed to water in cm2. A specific porosity of $\leq 1.0$ ml/min/cm$^2$ is considered an acceptable amount of leakage for an implantable vascular graft. Accordingly, for purposes of this invention, a substantially fluid-tight graft means a graft with a specific porosity, after impregnation with a sealant of the present invention, of $\leq 1.0$ ml/min/cm$^2$. Porosities meeting and exceeding the acceptable specific porosity criteria set forth above are achieved through the use of certain block copolymers described herein having polyether-polyester segments.

Implantable materials useful in the present invention can include, for example polymeric compositions, non-polymeric compositions and combinations thereof. The polymeric material can include, for example, olefin polymers including polyethylene, polypropylene, polyvinyl chloride, polytetrafluoroethylene, fluorinated ethylene propylene copolymer, polyvinyl acetate, polystyrene, poly (ethylene terephthalate), polyurethane, polyurea, silicone rubbers, polyamides, polycarbonates, polyaldehydes, natural rubbers, polyester copolymers, styrene-butadiene copolymers and combinations thereof. Non-polymeric implantable materials can include, for example, ceramics, metals, inorganic glasses, pyrolytic carbon and combinations thereof. The compositions set forth hereinabove for the implantable substrate material of the present invention are intended to be exemplary only and should not be construed to limit in any way the types of materials to which the present bioresorbable coatings can be applied.

As set forth above, these implantable materials are used to manufacture medical devices, such as for example, endoprostheses. Grafts, stents and combination graft-stent devices are contemplated. Preferably these medical devices are vascular or endovascular grafts. Useful vascular or endovascular grafts include those which are knitted, braided or woven textiles, and may have velour or double velour surfaces. Alteratively, the medical device can be manufactured from an extruded polymer, such as polytetrafluoroethylene (PTFE), polyethylene terephthalate (PET), fluorinated ethylene propylene copolymer (FEP), polyurethane, silicone and the like. Composite structures are also contemplated.

In another preferred embodiment, the medical device may be a catheter, a guidewire, a trocar, an introducer sheath or the like. When coated onto such devices, the composition of the present invention imparts increased bio-compatibility to one or more surfaces thereof. Furthermore, when the present composition includes a drug or bio-active agent, specific therapeutic effects can be imparted to the surfaces of such devices. Moreover, the hydrophilic region of the present composition can impart increased lubriciousness to the surfaces of, e.g., a guidewire or other similar device.

Thus, any medical device to which the bioresorbable coating composition can adhere can be used in conjunction with the present invention. Accordingly, the examples of implantable materials and medical devices set forth hereinabove are for purposes of illustration only and are not intended to limit the scope of the materials and devices to which the present bioresorbable coatings can be applied or otherwise associated therewith.

In another embodiment of the present invention, there is provided a process for forming a hydrogel. This process includes: (I) providing an aqueous emulsion of a water-insoluble copolymer which contains a bioresorbable region, a hydrophilic region, a plurality of crosslinkable functional groups per polymer chain and a crosslinking agent; and (ii) activating the crosslinking agent, as set forth previously. In this process, the crosslinkable functional groups can be, but are not limited to, olefinically unsaturated groups. As set forth previously, the crosslinking agent can be a free radical initiator, an azo or a peroxide composition. Still further, the crosslinking agent can be, for example, thermally or photochemically activated.

In yet another embodiment of the present invention, there is provided a process for forming a medical device coated with a hydrogel. As set forth previously, this hydrogel is formed from an aqueous emulsion which includes a water-insoluble copolymer. This copolymer includes a bioresorbable region, a hydrophilic region, a plurality of crosslinkable functional groups per polymer chain and a crosslinking agent. Accordingly, this process includes applying the hydrogel to the medical device and then activating the crosslinking agent in a humid environment.

Although, the crosslinking agent can be activated in both humid and non-humid environments, it is preferred that the activation take place in humid environments. Preferably, the humid environment contains from about 20% to about 100% water. More preferably, the humid environment contains from about 60% to about 100% water.

The hydrogels formed by this process can be packaged and stored in a variety of ways. For example, the hydrogel can be maintained in a hydrated state for an extended period of time. Alternatively, the hydrogel can be dehydrated and stored in an essentially desiccated state until use.

As set forth previously, a therapeutic agent, such as for example, a drug or bio-active agent can be added to the emulsion for targeted, timed release of such agents in the body. Examples of types of therapeutic agents which can be incorporated into the emulsion have been set forth above.

The following examples are set forth to illustrate the copolymer compositions of the present invention. These examples are provided for purposes of illustration only and are not intended to be limiting in any sense.

EXAMPLE 1

A polymer (Polymer A) according to the present invention was synthesized as follows:

125.0 gm poly(ethylene glycol-co-propylene glycol) (75 wt % ethylene glycol, $M_n$=12,000) was charged to a 4-necked reaction flask equipped with a Dean-Stark water trap, a water-cooled condenser, a thermometer, and a gas inlet/a gas outlet system which allowed for the controlled flow of nitrogen. While maintaining a nitrogen atmosphere, 660 ml anhydrous toluene was added to the flask and the mixture was heated and reflux was maintained for 3–4 hours. During this period any water present was collected in the Dean-Stark trap (approximately 10% of the original toluene was also removed during this azeotropic water removal). The flask was allowed to cool to room temperature and 30.4 gm d, 1-lactide was added to the flask followed by 50 mg of stannous 2-ethylhexanoate catalyst (1% solution in anhydrous toluene). The reaction mixture was heated to reflux for 6 hours and was allowed to cool to room temperature.

5.28 gm of triethylamine was added to the mixture. After 5 minutes of stirring, 4.72 gm of acryloyl chloride was slowly added to the flask. The mixture was then heated to reflux for 7 hours followed by cooling to room temperature. Unreacted acryloyl chloride was quenched with 15 ml of methanol. Approximately 110 mg of 4-methoxy phenol was added to the flask as a free-radical stabilizer.

The solution was filtered to remove triethylamine hydrochloride and the amount of solvent was reduced in vacuo to approximately half of the original volume. This solution was then precipitated into ether, filtered and the remaining solvent was removed in vacuo to afford the polymer as a viscous oil which is substantially water-insoluble.

EXAMPLE 2

Another polymer (Polymer B) according to the present invention was synthesized as set forth in Example 1 with the following exceptions. 60.07 gm of 1-lactide was substituted for the d, 1-lactide of Example 1 and the amount of stannous 2-ethylhexanoate was decreased to 40 mg. The resulting Polymer B was a waxy solid which was substantially water-insoluble.

EXAMPLE 3

Polymer C according to the present invention was synthesized as set forth in Example 1 with the following exceptions. The amount of d,1-lactide was increased to 71.2 gm, the amount of stannous 2-ethylhexanoate was decreased to 40 gm, the amount of acryl chloride was increased to 22.63 gm and the amount of triethylamine was increased to 25.63 gm. The resulting Polymer C was an oil which was substantially water-insoluble.

EXAMPLE 4

Polymer D according to the present invention was synthesized as set forth in Example 1 with the following exceptions. The amount of d,1-lactide was increased to 22.5 gm and the amount of stannous 2-ethylhexanoate was also decreased to 40 mg. The resulting Polymer D was a viscous oil that was substantially water-insoluble.

EXAMPLE 5

An aqueous emulsion (20% solids) was prepared by dispersing Polymer D and Vazo™ 044 (13.4 mg Vazo/1.0 gm. polymer) in water with rapid stirring. The mixture was transferred to a shallow Teflon™ mold (9cm×9 cm×1 cm), which was sealed with a glass cover plate and place in an oven at 60° C. for approximately 60 minutes.

The resulting hydrogel was demolded and dehydrated in vacuo to afford a thick elastic film with a hardness of Shore A=28. Stress-strain (Instron testing with crosshead speed =200 mm/min.), tensile strength at break ($T_b$)=50 psi (0.35 Mpa) and % elongation at break (%$E_B$)=585. The water uptake of this dehydrated hydrogel was determined as follows:

| time (hr.) | weight gm. | % weight gain |
|---|---|---|
| 0 | 0.2275 | |
| 1 | 1.9145 | 590 |
| 2 | 2.5295 | 812 |
| 24 | 3.5325 | 1174 |

EXAMPLE 6

A fabric suitable for use in medical procedures was coated with Polymer D of the present invention. In particular, a 1 inch ×3 inch rectangle of a knitted polyester medical fabric was impregnated by immersing it for 5.0 minutes in a degassed aqueous emulsion containing 1.0 gm of Polymer D and 13.4 mg. Vazo T 044 dispersed in 4.0 ml. de-ionized water. The impregnated fabric was then passed twice through a soft rubber wringer to remove excess emulsion. The impregnated fabric was then placed in an environmental chamber maintained at about 60–65° C. and 100% relative humidity under nitrogen for 60 minutes. The sample was then cooled to room temperature, washed twice (each wash was 15 minutes) with distilled water, then dried to constant weight.

EXAMPLE 7

The water porosity of the coated medical fabric of Example 6 was determined in a laboratory apparatus as described in AAMI Standards & Recommended Procedures, 1989, Reference Book; and in "Evaluation of Tissue and Prosthetic Vascular Grafts", p. 62, Charles Thomas, Publisher, Springfield, Ill., 1962. In the water porosity test, the coated medical fabric of Example 6 was placed over a hole, and a metal plate, containing a concentric hole of the same size, was clamped over the sample. Water was permitted to flow through the fabric, and the pressure was adjusted until the specific test pressure was reached. Porosity was calculated as follows:

Porosity=$Q/A$ where,

Q=flow rate through the sample in cc/minute @ 120 mm Hg, and

A=the cross-sectional area in cm$^2$ of the hole.

The following table sets forth the porosity data for the medical fabric coated with Polymer D.

Water Porosity of Hydrogel Coated Knitted Polyester Fabric

| Sample | Number of Coats | Sealant as wt % of Total Specimen | Porosity (ml/min./cm$^2$) |
|---|---|---|---|
| uncoated control | | | 559.0 |
| specimen 1 (20% solids) | 1 | 20.7 | 0.0 |
| specimen 2 (20% solids) | 1 | 21.0 | 2.6 |
| specimen 3 (20% solids) | 2 | 29.9 | 0.0 |
| specimen 4 (20% solids) | 3 | 19.1 | 9.4 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A covalently crosslinkable composition comprising an aqueous emulsion comprising about 20% by weight of a water-insoluble copolymer having (i) a bioresorbable region; (ii) a hydrophilic region; and (iii) a plurality of crosslinkable functional groups per polymer chain.

2. The composition of claim 1, wherein said copolymer has the following chemical structure:

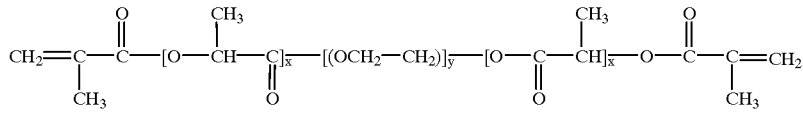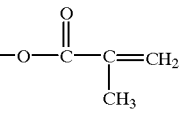

wherein x is from about 10 to about 50 and y is from about 50 to about 300.

3. The composition of claim 1, wherein the ratio of said bioresorbable region to said hydrophilic region is from about 10:1 to about 1:1 on a percent by weight basis.

4. The composition of claim 1, wherein said bioresorbable region is selected from the group consisting of poly(esters), poly(hydroxy acids), poly (lactones), poly (amides), poly (ester-amides), poly (amino acids), poly(anhydrides), poly (orthoesters), poly(carbonates), poly(phosphazines), poly (phosphoesters), poly(thioesters), polysaccharides, polylactic acid, polyglycolic acid, polycaproic acid, polybutyric acid, polyvaleric acid and copolymers and mixtures thereof.

5. The composition of claim 1, wherein said hydrophilic region is selected from the group consisting of polyethers, polyalkylene oxides, polyols, poly(vinylpyrrolidine), poly (vinyl alcohol), poly(alkyl oxazolines), polysaccharides, carbohydrates, peptides, proteins and copolymers and mixtures thereof.

6. The compositions of claim 1, wherein said copolymer is selected from the group consisting of di-block copolymers, tri-block copolymers, and star copolymers.

7. The composition of claim 6, wherein said tri-block copolymer has the general formula:

xABAx wherein A is the bioresorbable region, B is the hydrophilic region, and x is the crosslinkable functional group.

8. A process for forming a hydrogel, comprising:

a. providing an aqueous emulsion comprising about 20% by weight of a water-insoluble covalently crosslinkable copolymer having (I) a bioresorbable region; (ii) a hydrophilic region; and (iii) a plurality of crosslinkable functional groups per polymer chain; and b. effecting crosslinking of said cross-linkable functional groups.

9. The process of claim 8, wherein said copolymer has the following chemical structure:

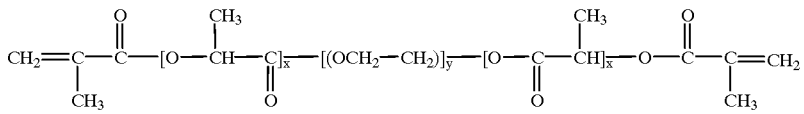

wherein x is from about 10 to about 50 and y is from about 50 to about 300.

10. The process of claim 8, wherein the ratio of said bioresorbable region to said hydrophilic region is from about 1 0:1 to about 1:1 on a percent by weight basis.

11. The process of claim 8, wherein said bioresorbable region is selected from the group consisting of poly(esters), poly(hydroxy acids), poly (lactones), poly (amides), poly (ester-amides), poly (amino acids), poly(anhydrides), poly (orthoesters), poly(carbonates), poly(phosphazines), poly (phosphoesters), poly(thioesters), polysaccharides, polylactic acid, polyglycolic acid, polycaproic acid, polybutyric acid, polyvaleric acid and copolymers and mixtures thereof.

12. The process of claim 8, wherein said copolymer is selected from the group consisting of di-block copolymers, tri-block copolymers, and star copolymers.

13. The composition of claim 12, wherein said tri-block copolymer has the general formula:

xABAx wherein A is the bioresorbable region, B is the hydrophilic region, and x is the crosslinkable functional group.

14. A medical device having on at least one surface thereof a bioresorbable coating composition, said composition comprising an aqueous emulsion comprising about 20% by weight of a water-insoluble copolymer having (I) a bioresorbable region; (ii) a hydrophilic region; and (iii) a plurality of crosslinkable functional groups per polymer chain.

15. The medical device of claim 14, wherein said hydrogel is useful as a drug or bio-active agent delivery vehicle.

16. The medical device of claim 15, wherein said drug or bio-active agent is selected from the group consisting of thrombo-resistant agents, antibiotic agents, anti-tumor agents, antiviral agents, anti-angiogenic agents, angiogenic agents, anti-inflammatory agents, cell cycle regulating agents, and chemically modified equivalents and combinations thereof.

17. The medical device of claim 16, wherein said thrombo-resistant agents are selected from the group consisting of heparin, heparin sulfate, hirudin, hyaluronic acid, chondroitin sulfate, dermatan sulfate, keratan sulfate, lytic agents, urokinase, streptokinase, and chemically modified equivalents and combinations thereof.

18. The medical device of claim 16, wherein said antibiotic agents are selected from the group consisting of penicillins, cephalosporins, vancomycins, aminoglycosides, quinolones, polymyxins, erythromycins, tetracyclines, chloramphenicols, clindamycins, lincomycins, sulfonamides, and chemically modified equivalents and combinations thereof.

19. The medical device of claim 16, wherein said anti-tumor agents are selected from the group consisting of paclitaxel, mechlorethamine, chlorambucil, cyclophosphamide, melphalan, ifosfamide, methotrexate, 6-mercaptopurine, 5-fluorouracil, cytarabine, vinblastine, vincristine, etoposide, doxorubicin, daunomycin, bleomycin, mitomycin, carmustine, lomustine, cisplatin, interferon, asparaginase, tamoxifen, flutamide, and chemically modified equivalents and combinations thereof.

20. The medical device of claim 16, wherein said antiviral agents are selected from the group consisting of amantadines, rimantadines, ribavirins, idoxuridines, vidarabines, trifluridines, acyclovirs, ganciclovirs, zidovudines, foscarnets, interferons, and chemically modified equivalents and combinations thereof.

21. The medical device of claim 14 formed from an implantable material.

22. The medical device of claim 21, wherein said implantable material is selected from the group consisting of polymeric compositions, non-polymeric compositions and combinations thereof.

* * * * *

UNITED STATES PATENT AND TRADEMARK OFFICE
CERTIFICATE OF CORRECTION

PATENT NO. : 6,403,758 B1
DATED : June 11, 2002
INVENTOR(S) : Loomis, Gary L.

It is certified that error appears in the above-identified patent and that said Letters Patent is hereby corrected as shown below:

<u>Column 5,</u>
Line 20, incorrectly reads "...10:1 to about 1;1, on...". should read
-- ...10:1 to about 1:1, on... --.

<u>Column 13,</u>
Line 13, incorrectly reads "...1 0:1 to about 1:1...". should read
-- ...10:1 to about 1:1... --.

Signed and Sealed this

Twenty-seventh Day of May, 2003

JAMES E. ROGAN
*Director of the United States Patent and Trademark Office*